United States Patent [19]
Inman et al.

[11] Patent Number: 5,818,578
[45] Date of Patent: Oct. 6, 1998

[54] POLYGONAL PLANAR MULTIPASS CELL, SYSTEM AND APPARATUS INCLUDING SAME, AND METHOD OF USE

[75] Inventors: Ronald S. Inman, Lyons; James McAndrew, Lockport, both of Ill.

[73] Assignee: American Air Liquide Inc., Walnut Creek, Calif.

[21] Appl. No.: 711,504

[22] Filed: Sep. 10, 1996

Related U.S. Application Data

[63] Continuation-in-part of Ser. No. 634,436, Apr. 18, 1996, abandoned.

[60] Provisional application No. 60/005,013 Oct. 10, 1995.

[51] Int. Cl.⁶ .................................................. G01N 1/10
[52] U.S. Cl. ........................... 356/246; 356/437; 356/440
[58] Field of Search ..................... 356/432–444, 356/244, 246, 236; 250/343, 573, 576, 353; 359/850, 858, 861

[56] References Cited

U.S. PATENT DOCUMENTS

| | | |
|---|---|---|
| 3,524,066 | 8/1970 | Blakkan . |
| 3,994,603 | 11/1976 | Paschedag ............................... 356/434 |
| 4,812,665 | 3/1989 | Puumalainen et al. . |
| 4,934,816 | 6/1990 | Silver et al. . |
| 4,937,461 | 6/1990 | Traina . |
| 4,990,780 | 2/1991 | Lee et al. . |
| 5,024,526 | 6/1991 | Von Rediovtz ........................ 356/339 |
| 5,045,703 | 9/1991 | Wieboldt et al. . |

(List continued on next page.)

FOREIGN PATENT DOCUMENTS

| | | |
|---|---|---|
| 0015170 | 9/1980 | European Pat. Off. . |
| 0647845 | 4/1995 | European Pat. Off. . |
| 0 706 042 | 4/1996 | European Pat. Off. . |
| 0738887 | 4/1996 | European Pat. Off. . |
| 25 04 300 | 11/1975 | Germany . |
| 3633931 | 4/1988 | Germany . |
| 4214840 | 11/1993 | Germany . |
| 2075213 | 11/1981 | United Kingdom . |
| 2165640 | 4/1986 | United Kingdom . |
| WO90/00732 | 1/1990 | WIPO . |
| WO94/24528 | 10/1994 | WIPO . |

OTHER PUBLICATIONS

T. A. Hu et al, "Improved Multipass Optics for Diode Laser Spectroscopy", Review of Scientific Instruments, vol. 64, No. 12, Dec. 1993, pp. 3380–3383.

Patent Abstracts of Japan, vol. 6, No. 59, JP 57–1953, Jan. 1982.

Kaur et al, "Multipass cell for molecular beam absorption spectroscopy," Applied Optics, Jan. 1, 1990, vol. 29, No. 1, pp. 119–124.

Fried et al., "Versatile Integrated Tunable Diode Laser System for High Precision: Application for Ambient Measurements of OCS", Applied Optics, vol. 30, No. 15, May 20, 1991, pp. 1916–1932.

(List continued on next page.)

*Primary Examiner*—Hoa Q. Pham
*Attorney, Agent, or Firm*—Burns, Doane, Swecker & Mathis, L.L.P.

[57] ABSTRACT

Provided is a novel polygonal planar multipass cell and method of use for absorption spectroscopy. The cell comprises a sample region circumscribed by a plurality of walls. Each wall has a light reflective surface facing the sample region, and each wall is connected to at least one other wall so as to form in cross section substantially a polygon. At least one side of the polygon has a light entry/exit port therein, and the entry/exit port contains a light transmissive window which has a surface facing the sample region. The window is disposed so as to seal the cell in the circumferential direction. The cell has a central axis parallel to the light reflective surfaces of the walls and the surface of the light transmissive window which face the sample region. The cell can be used to measure molecular gas impurities in a sample. Particular applicability is found in semiconductor processing.

42 Claims, 5 Drawing Sheets

U.S. PATENT DOCUMENTS

| | | |
|---|---|---|
| 5,065,025 | 11/1991 | Doyle . |
| 5,173,749 | 12/1992 | Tell et al. . |
| 5,220,402 | 6/1993 | Harvey .................................. 356/440 |
| 5,241,851 | 9/1993 | Tapp et al. . |
| 5,294,289 | 3/1994 | Heinz et al. . |
| 5,331,409 | 7/1994 | Thurtell et al. . |
| 5,352,902 | 10/1994 | Aoki . |
| 5,453,621 | 9/1995 | Wong . |
| 5,459,574 | 10/1995 | Lee et al. . |
| 5,485,276 | 1/1996 | Bien et al. . |
| 5,517,314 | 5/1996 | Wallin . |
| 5,536,359 | 7/1996 | Kawada et al. . |
| 5,550,636 | 8/1996 | Hagans et al. . |
| 5,561,527 | 10/1996 | Krone-Schmidt et al. . |
| 5,578,829 | 11/1996 | Talasek et al. . |

OTHER PUBLICATIONS

May, "Correlation–Based Technique for Automated Tunable Diode Laser Scan Stabilization", Rev. Sci. Instrum., vol. 63, No. 5, May 1992, pp. 2922–2926.

Eng et al., "Tunable Diode Laser Spectroscopy: An Invited Review", Optical Engineering, Nov./Dec. 1980, vol. 19, No. 6, pp. 945–960.

Lundqvist et al., "Measurements of Pressure–Broadening Coefficients of NO and $O_3$ Using A Computerized Tunable Diode Laser Spectrometer", Applied Optics, vol. 21, No. 17, Sep. 1, 1982, pp. 3109–3113.

Ahlberg et al., "IR–Laser Spectroscopy for Measurement Applications in the Industrial Environment", TR 85170, Dec. 85.

Höjer et al., "Measurements of Electric Field Strength In Gas Insulated High–Voltage Components Using Infrared Diode Laser Absorption Spectroscopy", Applied Optics, vol. 25, No. 17, Sep. 1, 1986; pp. 2984–2987.

Cassidy, "Trace Gas Detection Using 1.3$\mu$m InGaAsP Diode Laser Transmitter Modules", Applied Optics, vol. 27, No. 3, Feb. 1, 1988, pp. 610–614.

Mitsui et al., "Development of New APIMS for the Detection of Trace Impurities in Special Gases", Proceedings of the 40th Annual Technical Meeting of the IES, Chicago, pp. 246–253 (1994).

Herriott et al., "Folded Optical Delay Lines", Applied Optics, vol. 4, No. 8, pp. 883–889 (Aug. 1965).

White, "Long Optical Paths of Large Aperture", J. Opt. Soc. Am., vol. 32 (1942), pp. 285–288.

Atkinson, "High Sensitivity Detection of Water Via Intracavity Laser Spectroscopy," Microcontamination Conference Proceedings, pp. 98–111 (1994).

Borden, "Monitoring Vacuum Process Equipment: In Situ Monitors—Design and Specification," Microcontamination, vol. 9, No. 1, pp. 43–47 (1991).

Davies et al, "Infrared Laser Diagnostics in Methane Chemical–Vapor–Deposition Plasmas," Journal of Applied Physics, vol. 71, No. 12, Jun. 15, 1992, pp. 6125–6135.

Dreyfus et al, "Optical Diagnostics of Low Pressure Plasmas," Pure & Appl. Chem., vol. 57, No. 9, pp. 1265–1276 (1985).

Feher et al, "Tunable Diode Laser Monitoring of Atmospheric Trace Gas Constituents," Spectrochimica Acta, A 51, pp. 1579–1599 (1995).

Fried et al, "Application of Tunable Diode Laser Absorption for Trace Stratospheric Measurements of HCL: Laboratory Results," Applied Optics, vol. 23, No. 11, Jun. 1984, pp. 1867–1880.

Grisar et al, "Fast Sampling Devices for Dynamic Exhaust Gas Analysis," *Proceedings of the 24th ISATA International Symposium on Automotive Technology and Automation*, 20 May 1991, pp. 283–287.

Inman et al, "Application of Tunable Diode Laser Absorption Spectroscopy to Trace Moisture Measurements in Gases," Analytical Chemistry, vol. 66, No. 15, pp. 2471–2479.

Jasinski et al, "Detection of $SiH_2$ in Silane and Disilane Glow Discharges by Frequency Modulation Absorption Spectroscopy," Applied Physics Letters, vol. 44, No. 12, Jun. 15, 1984, pp. 1155–1157.

May, "Computer Processing of Tunable Diode Laser Spectra," Applied Spectroscopy, vol. 43, No. 5, 1989, pp. 834–839.

May et al, "Data Processing and Calibration for Tunable Diode Laser Harmonic Absorption Spectrometers," J. Quant. Spectrosc. Transfer, vol. 49, No. 4, pp. 335–347, 1993, pp. 335–347.

Mucha et al., "Infrared Diode Laser Determination of Trace Moisture in Gases", ISA Transactions, vol. 25, No. 3, pp. 25–30 (1986).

Podolske et al, "Airborne Tunable Diode Laser Spectrometer for Trace–Gas Measurement in the Lower Stratosphere," Applied Optics, vol. 32, No. 27, pp. 5324–5333.

Pokrowsky et al, "Sensitive Detection of Hydrogen Chloride by Derivative Spectroscopy with a Diode Laser," Optical Engineering, vol. 23, No. 1 (1984), pp. 088–091.

Riris et al, "Design of an Open Path Near–Infrared Diode Laser Sensor: Application to Oxygen, Water, and Carbon Dioxide Vapor Detection," Applied Optics, vol. 33, No. 30, Oct. 20, 1994, pp. 7059–7066.

Smoak, Jr. et al, "Gas Control Improves EPI Yield", Semiconductor Int'l ., pp. 87–92 (1990).

Staab, "Industrielle Gasanalyse Industrial Gas Analysis," Technisches Messen, vol. 61, No. 3, Mar. 1, 1994, pp. 133–137.

Webster et al, "Aircraft (ER–2) Laser Infrared Absorption Spectrometer (ALIAS) for In–Situ Stratospheric Measurements of HCI, $N_2O$, $CH_2$, $NO_2$, and $HNO_3$," Applied Optics, vol. 33, No. 3, Jan. 20, 1994, pp. 454–472.

Wilson, "Modulation Broadening of NMR and ESR Line Shapes", J. App. Phys., vol. 34, No. 11, pp. 3276–3285 (1963).

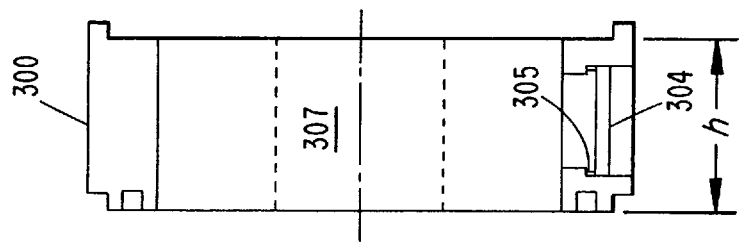
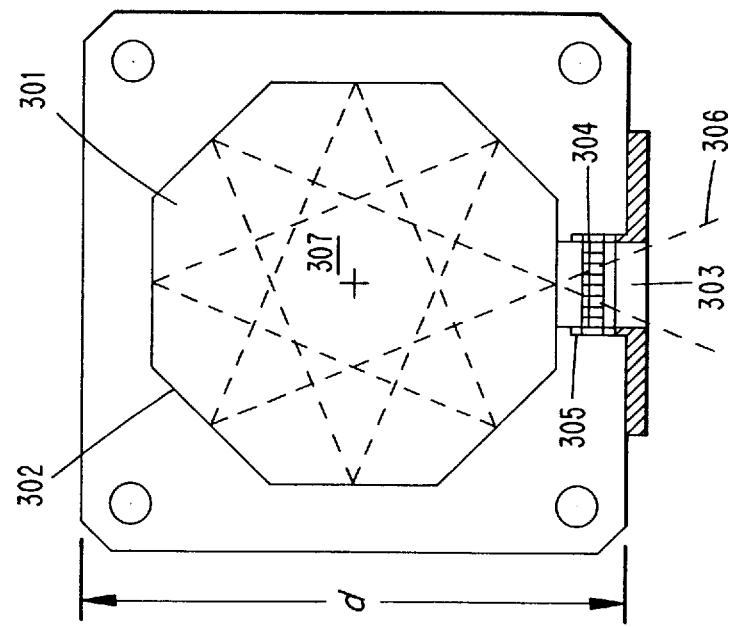

POLYGONAL PLANAR MULTIPASS CELL, SYSTEM AND APPARATUS INCLUDING SAME, AND METHOD OF USE

CROSS REFERENCE TO RELATED APPLICATIONS

This application is a Continuation-in-Part of application Ser. No. 08/634,436 filed Apr. 18, 1996 now abandoned, and this application claims the benefit of U.S. provisional application No. 60/005,013 filed Oct. 10, 1995.

BACKGROUND OF THE INVENTION

1. Field of the Invention

The present invention relates to a polygonal planar multipass cell useful in absorption spectroscopy. The present invention also relates to a system for detecting gas phase molecular species in a sample and a semiconductor processing apparatus which comprise the same.

2. Description of the Related Art

Semiconductor integrated circuits (ICs) are manufactured by a series of processes, many of which involve the use of gaseous materials. Included among such processes are etching, diffusion, chemical vapor deposition (CVD), ion implantation, sputtering and rapid thermal processing. In these processes, contact is made between a semiconductor substrate and materials in the gas phase. As a result of the extremely fine features of the IC devices, parts per billion (ppb) and lower levels of all impurities in the gases contacting the semiconductor substrates are usually considered necessary in order to minimize yield loss. Among the potential impurities, moisture is extremely difficult to eliminate, and it adversely affects many semiconductor manufacturing processes.

In atmospheres of nitrogen, argon and hydrogen several analytical techniques, most notably atmospheric pressure ionization mass spectroscopy (APIMS), deliver the requisite sensitivity for measuring moisture and other impurities. However, APIMS is not compatible with many reactive gases. Although its operation in $SiH_4$ has been demonstrated (See Y. Mitsui et al., Proceedings of the 40th Annual Technical Meeting of the IES, Chicago 1994, pp. 246–254, IES 1994), APIMS is difficult to use in practice. The need exists for extremely sensitive techniques compatible with a wider range of gases. Fourier Transform Infrared spectroscopy (FT-IR) is currently the technique of choice for reactive gases in many gas analysis laboratories. Unfortunately FT-IR seems unable to deliver the 1 ppb sensitivity that is required in the semiconductor manufacturing industry. In addition, the spectral resolution achievable by FT-IR is limited, which makes it more difficult to detect impurities in the presence of other infrared absorbing molecules. It is also difficult to devise an extremely compact FT-IR.

Tunable diode laser absorption spectroscopy (TDLAS) is a technique having considerable flexibility and sensitivity, which has become widely used in environmental monitoring, spectroscopy, chemical kinetics, and the like. TDLAS lends itself to the construction of a compact sensor, as its component parts can be made very small. The sensitivity of detection of gas phase molecular species by absorption spectroscopy increases as the length of the light path through the sample increases, for constant pressure and concentration. The intensity of light reaching the detector is given by Beer's Law:

$$I = I_o \cdot e^{-\alpha l c P}$$

where $I_o$, is the intensity of the incident radiation, $\alpha$ is the absorptivity, l is the pathlength through the sample, c is the concentration of the impurity in the sample (by volume), and P is the total pressure of the sample. For small absorptions, the amount of light absorbed is given by $$I - I_o = \alpha l c P$$

In order to make l large, it is frequently impractical to place the light source and detector very far apart and so "folded" light paths are often used, in which mirrors reflect the light back and forth through the sample gas many times.

As shown in FIG. 1, the cell of White 100 is the best known folded path cell design and uses a single curved mirror 101 mounted at one end and a pair of curved mirrors 102 mounted at the opposite end of a usually cylindrical gas sample cell. Herriott's design 200, shown in FIG. 2, is often preferred for TDLAS. This design uses two curved mirrors 201 mounted at opposite ends of a usually cylindrical gas sample cell 202. Additionally, "folded pass cells" exist in which the light does not pass repeatedly through the same gas volume but instead a long, single-pass sample cell is folded back on itself to give a compact geometry, using mirrors to transport the light around the folds in the cell. Finally, simple multi-pass arrangements are often used, including for a example a straightforward "retroreflector" which is a single mirror directing the light back to a detector mounted adjacent to the source and pairs of parallel plane mirrors which allow light striking one mirror at a slight angle to reflect back and forth between the two mirrors until it reaches the end of one mirror or the other, such as described in U.S. Pat. No. 3,524,066.

U.S. Pat. No. 5,173,749 also describes a non-planar multipass cell for spectroscopic measurement of a gas sample. This cell consists of a cylindrical measurement tube which is divided into twelve 30 degree segments, with each segment containing a dielectric mirror for reflecting a light beam. A light beam inlet and an exit are disposed at opposite ends of the cell. The beam is reflected by the segments inside the measurement cell, with the beam pattern automatically repeating itself as it passes upwardly through the cell between the inlet and exit.

The multipass cell designs of White and Herriott are well-suited to analysis in cylindrical sample cells, however, they require curved mirrors of equal extension in both directions perpendicular to the light path. This is not always convenient and is costly to manufacture. The design of the cell set forth in U.S. Pat. No. 5,173,749 prevents minimization of the cell height due to the path of the light beam extending from one end of the cell to the opposite end. In light of these characteristics, the prior art cell designs are unsuitable for use with many designs of semiconductor processing equipment. For example, when it is desired to retrofit a sensor using a multipass light path to detect molecules in the gas exhausted from a vacuum chamber which forms a portion of a semiconductor processing apparatus, a vacuum pump is connected to the vacuum chamber so as to exhaust the chamber through a large opening. In such an apparatus, it is desirable to mount the multipass cell between the vacuum chamber and the pump while displacing the pump mount as little as possible. Therefore, the multipass cell should have a dimension as small as possible in the direction of gas flow through the cell. The need for a small displacement of the vacuum pump arises because other equipment is typically mounted in close proximity to the pump, and there is typically little room to move the pump without redesigning the entire process tool. This multipass cell is extremely suitable for use with TDLAS to obtain a compact measurement system.

To meet the requirements of the semiconductor processing industry and to overcome the disadvantages of the prior art, it is an object of the present invention to provide a novel cell useful in absorption spectroscopy which will allow for accurate in situ determination of gas phase molecular impurities in samples without having to redesign existing semiconductor processing equipment.

It is a further object of the present invention to provide an absorption spectroscopy system for detecting gas phase molecular species in a sample using the inventive cell.

It is further an object of the present invention to provide a semiconductor processing apparatus which includes an absorption spectroscopy system for detecting gas phase molecular impurities in a sample at a level at least as low as in the ppb range.

It is further an object of the present invention to provide a method of detecting gas phase impurities by absorption spectroscopy using the inventive cell.

Other objects and aspects of the present invention will become apparent to one of ordinary skill in the art on a review of the specification, drawings and claims appended hereto.

SUMMARY OF THE INVENTION

According to a first aspect of the present invention, a novel polygonal planar multipass cell useful in absorption spectroscopy is provided. The cell comprises a sample region circumscribed by a plurality of walls. Each wall has a light reflective surface facing the sample region, and each wall is connected to at least one other wall so as to form in cross section substantially a polygon. At least one side of the polygon has a light entry/exit port therein, and each entry/exit port contains a light transmissive window which has a surface facing the sample region. Each window is disposed so as to seal the cell in the circumferential direction. The cell has a central axis parallel to the light reflective surfaces of the walls and the surface of each light transmissive window which face the sample region. The polygonal planar multipass cell of the present invention permits accurate in situ detection of gas phase molecular species in a sample.

According to a second aspect of the invention, a system for detecting gas phase molecular species in a sample is provided. The system includes a polygonal planar multipass cell as described above with reference to the first aspect of the invention. The inventive system further comprises a light source for directing a light beam through one of the at least one light transmissive windows into the cell and a main detector for measuring the light beam exiting the cell through one of the at least one light transmissive windows. A sample gas flows through the sample region in a direction parallel to the cell central axis.

According to a third aspect of the invention, a semiconductor processing apparatus is provided. The apparatus comprises a vacuum chamber in communication with a vacuum pump for evacuating the vacuum chamber, and the inventive system as described above with reference to the second aspect of the invention.

A fourth aspect of the invention is a method of detecting gas phase impurities using the inventive sample cell, system and apparatus.

BRIEF DESCRIPTION OF THE DRAWINGS

The objects and advantages of the invention will become apparent from the following detailed description of the preferred embodiments thereof in connection with the accompanying drawings in which like numerals designate like elements, and in which:

FIG. 3A is a cross sectional view of the polygonal planar multipass cell according to one embodiment of the present invention;

FIG. 3B is a longitudinal sectional view of the polygonal planar multipass cell illustrated in FIG. 1;

DETAILED DESCRIPTION OF THE PREFERRED EMBODIMENTS OF THE INVENTION

Figure 1:
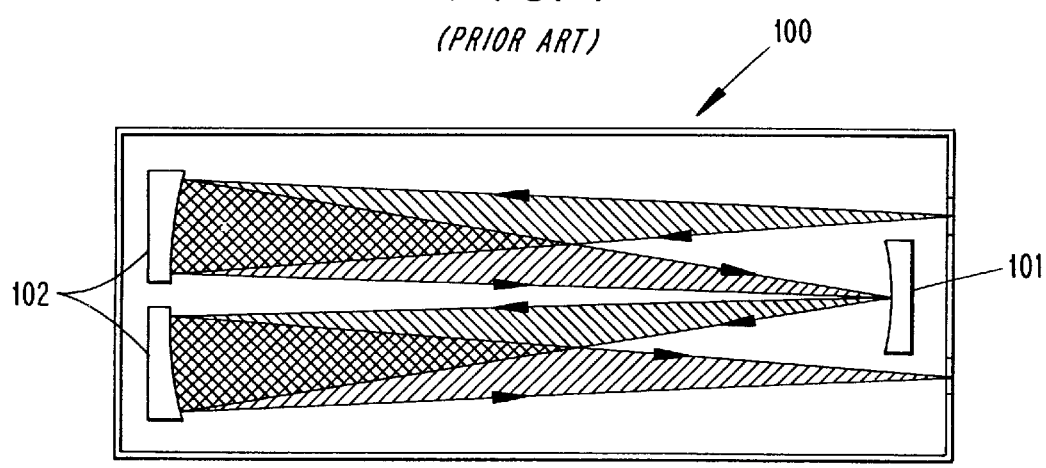
FIG. 1 is a conventional absorption spectroscopy cell according to the White design.
Figure 2:
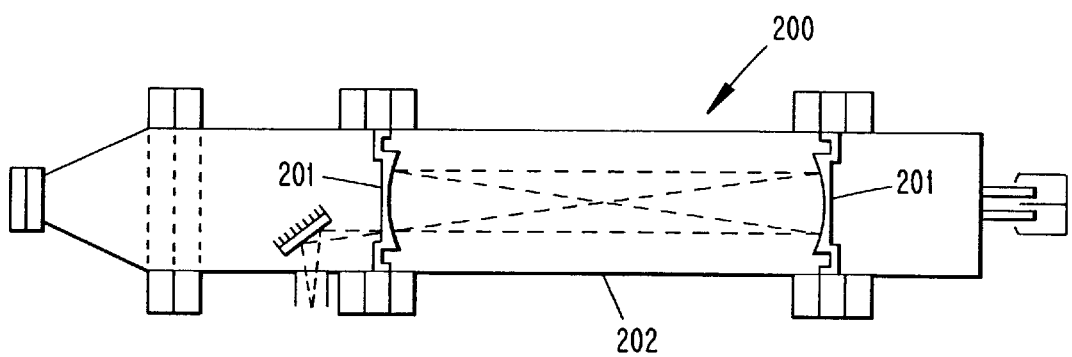
FIG. 2 is a conventional absorption spectroscopy cell according to the Herriott design.

Referring to the drawings, FIGS. 3A and 3B illustrate a cross sectional view and longitudinal sectional view, respectively, of a preferred polygonal planar multipass cell 300 useful in absorption spectroscopy according to the invention. In this embodiment, a sample region 301 is circumscribed by a plurality of walls 302 which have light reflective surfaces facing the sample region 301. The light reflective surfaces are preferably polished metal. As a high reflectivity of these surfaces is desirable, the surfaces can be coated with one or more layers of a reflective material such as gold, other metallic layers or a highly reflective dielectric coating. In order to enhance the reflectivity thereof. Moreover, to minimize the adverse effects created by deposits formed on the light reflective surfaces, one or more heaters for heating the light reflective surfaces can also be provided.

Each wall 302 of the cell is connected to at least one other wall so as to form in cross section substantially a polygon. The polygon is preferably a regular polygon, and can have any number of walls. An octagon is the preferred geometry of the polygon. At least one side of the polygon has a light entry/exit port 303 therein for allowing a light beam to pass into and/or out of the cell. The entry/exit port 303 contains a light transmissive window 304 which has a surface facing the sample region 303. It is through the light transmissive window(s) that a light beam is directed into the cell to the sample region and through which the beam exits the cell. Thus, the light beam can enter and exit the cell through the same or different windows, and the windows can be disposed on the same or different sides of the cell. Suitable light transmissive materials for the window are known to those skilled in the art.

The light transmissive window 304 seals the cell in the circumferential direction. To form a seal between the window and cell, a sealing means such as an O-ring 305 or other suitable structure can be used. Sealing the cell in this manner makes possible the measurement of gas samples at low pressure, i.e., at vacuum conditions. The light transmissive window 304 can additionally be provided with a coating layer on a surface opposite the surface facing the sample region for reflecting a portion of a light beam 306. As will be explained below, subtracting the signal due to the reflected portion of the beam from that of the transmitted portion results in more accurate absorption measurements. Among the commercially available coating materials, metallic coatings are preferred. The cell further has a central axis 307 which is parallel to the light reflective surfaces of the wall and the surface of the light transmissive window 304 which face the sample region 307.

It is preferred that the light reflecting surface of each wall 302 is substantially planar. Because the inventive cell design does not require curved mirrors such as are present in the prior art cells, the cell according to the present invention is inexpensive to manufacture relative to the prior art structures. Furthermore, the walls are arranged such that a light beam entering the cell remains in substantially the same plane while inside the cell. Consequently, the cell can be made arbitrarily small in directions parallel and perpendicular to the plane of propagation of the light, subject only to the diameter of the light beam and the geometrical constraints imposed by the window(s) through which the light beam enters and exits the chamber. This aspect of the invention makes it particularly well suited for use in existing semiconductor processing apparatus.

The walls are preferably arranged such that a light beam entering the cell is reflected from the light reflective surface of one wall to the light reflective surface of another wall, such that the light beam is reflected from each wall at least once prior to exiting the cell through the entry/exit port. The beam residence time and effective pathlength in the cell sample area is thereby extended.

In FIG. 3B, the cell height h, measured in a direction parallel to the cell central axis is in the range of from approximately 1 to 5 cm. Cell diameter d, measured in a direction perpendicular to the cell central axis, can be slightly larger than the diameter of the vacuum pump inlet, and is preferably in the range of from about 5 to 40 cm. The cell is of an open design, wherein the sample region circumscribed by the walls and light transmissive window preferably extends throughout the entire height of the cell. This configuration allows the sample to pass through the cell in a direction parallel to the cell central axis, which makes the cell particularly well suited for in situ measurements in semiconductor processing apparatus.

Figure 4A:
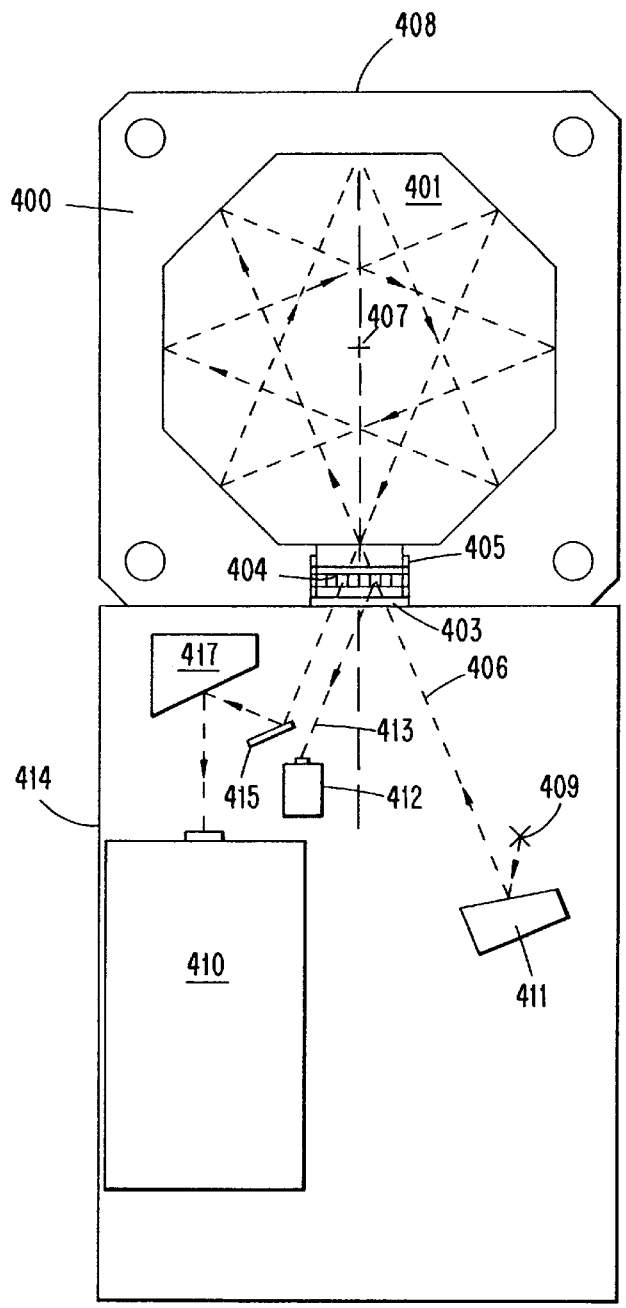
FIG. 4A is a cross sectional view of a system for detecting gas phase molecular species in a sample according to one embodiment of the present invention.
Figure 4B:
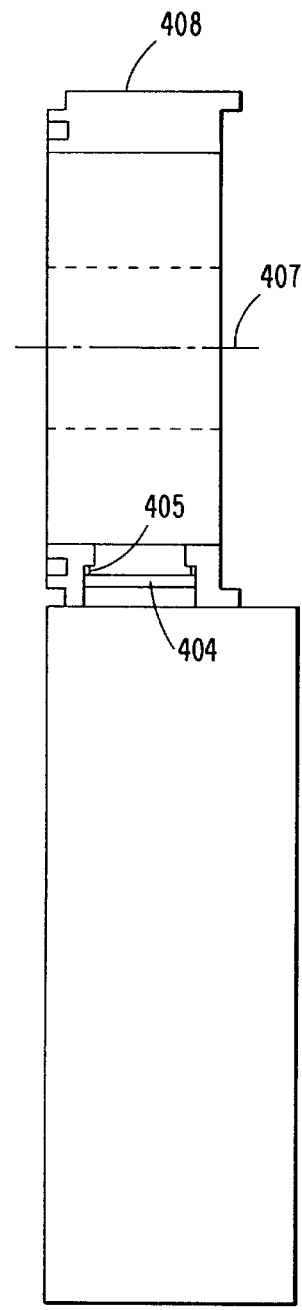
FIG. 4B is a longitudinal sectional view of the system illustrated in FIG. 4A.

FIGS. 4A and 4B depict a cross sectional view and longitudinal sectional view, respectively, of an inventive system 408 for detecting gas phase molecular species in a sample by absorption spectroscopy. While the inventive cell can be used for any absorption spectroscopy technique, it is preferably used in tunable diode laser absorption spectroscopy (TDLAS). This system includes a cell 401 as described above with reference to FIGS. 3A and 3B. Additionally, the system includes a light source 409, preferably a diode laser, for directing a light beam 406 through the light transmissive window 404 into the cell 401. To measure the light beam 406 which exits the cell through the light transmissive window 404, the system 408 further includes a main detector 410, which can be a photodiode.

Any molecular impurity of interest can be detected, subject only to the availability of a suitable light source. For example, water vapor, nitric oxide, carbon monoxide and methane or other hydrocarbons can be detected by measuring the attenuation of light from a diode laser source which emits light of a wavelength characteristic of the impurity.

Laser light sources which emit light in spectral regions where the molecules of interest absorb most strongly lead to improvements in measurement sensitivity. In particular, light sources which emit at wavelengths longer than about 2 $\mu$m are preferred, since many of the molecular impurities of interest have strong absorption bands in this region.

Any suitable wavelength-tunable light source can be used. Of the currently available light sources, diode laser light sources are preferred because of their narrow linewidth (less than about $10^{-3} cm^{-1}$) and relatively high intensity (about 0.1 to several milliwatts) at the emission wavelength.

Examples of diode lasers include Pb-salt and GaAs-type diode lasers. The Pb-salt-type laser requires cryogenic temperatures for operation and emits infrared light (i.e., wavelength greater than 3 $\mu$m), while the GaAs-type diode laser can operate at close to room temperature and emits in the near infrared region (0.8–2 $\mu$m).

Recently, diode lasers which include Sb in addition to GaAs (or other pairs of III–V compounds such as AsP) have been described (see, "Mid-infrared wavelengths enhance trace gas sensing," R. Martinelli, Laser Focus World, March 1996, p. 77). These diodes emit light of a wavelength greater than 2 $\mu$m while operating at $-87.8°$ C. While such a low temperature is not convenient, it compares favorably with the cryogenic temperatures (less than $-170°$ C.) required by Pb-salt lasers. Operation of similar lasers at 4 $\mu$m and 12° C. has also been reported (see, Lasers and Optronics, March 1996). Diode lasers of the above described type will most preferably operate at temperatures of at least $-40°$ C. Use of a thermoelectric cooler for temperature control at such temperatures makes these light sources less complicated than the lower temperature diode systems. To make use of these lasers more desirable, improvement in the optical properties over current levels is important. For example, single mode diodes (i.e., diodes whose emission at fixed temperature and drive current is at a single wavelength with emission at other wavelengths at least 40 dB less intense) should be available.

Suitable light sources for use in the invention are not limited to the above described diode lasers. For example, other types of lasers which are similarly sized and tunable by simple electrical means, such as fiber lasers and quantum cascade lasers, are envisioned. The use of such lasers as they become commercially available is envisioned.

The system can further include at least one first mirror 411 for reflecting the light beam 406 from the light source 409 through the light transmissive window 404 into the cell 401, and at least one second mirror 415, 417 for reflecting the light beam exiting the cell to the main detector 410. The mirror 411 is preferably curved in order to collimate the light beam as the light from the diode laser source is divergent. Likewise, the mirror 417 is preferably curved in order to focus the parallel light beam on the detector 410. A second detector 412, which can also be a photodiode, for measuring a portion of the light beam 413 which is reflected from the light transmissive window 404 as well as means for subtracting this reference signal from a measurement obtained by the main detector can optionally be provided in the system. An operational amplifier in a configuration such as described in the literature (See, e.g., Moore, J. H. et al "Building Scientific Apparatus", Addison Wesley, London, 1983) can act as the means for subtracting the reference signal.

The reflected light does not show any absorption by the molecules of interest in the sample region, and therefore provides a reference signal. By subtracting the reference signal from that of the light which passes through the cell (which is measured by the main detector), variations in the light source can be compensated for. This also allows for enhanced sensitivity to signal changes due to molecules in the system chamber 407. While "dual beam" techniques using subtraction of a reference beam are well-known they usually require a dedicated beam-splitter, i.e., an optical element whose only function is to divide the light beam. According to the present invention, the entrance window to the chamber can provide this function without the need for any additional components. The ratio of transmitted to reflected light at this window can be controlled by use of an appropriate coating for the window.

Figure 6:
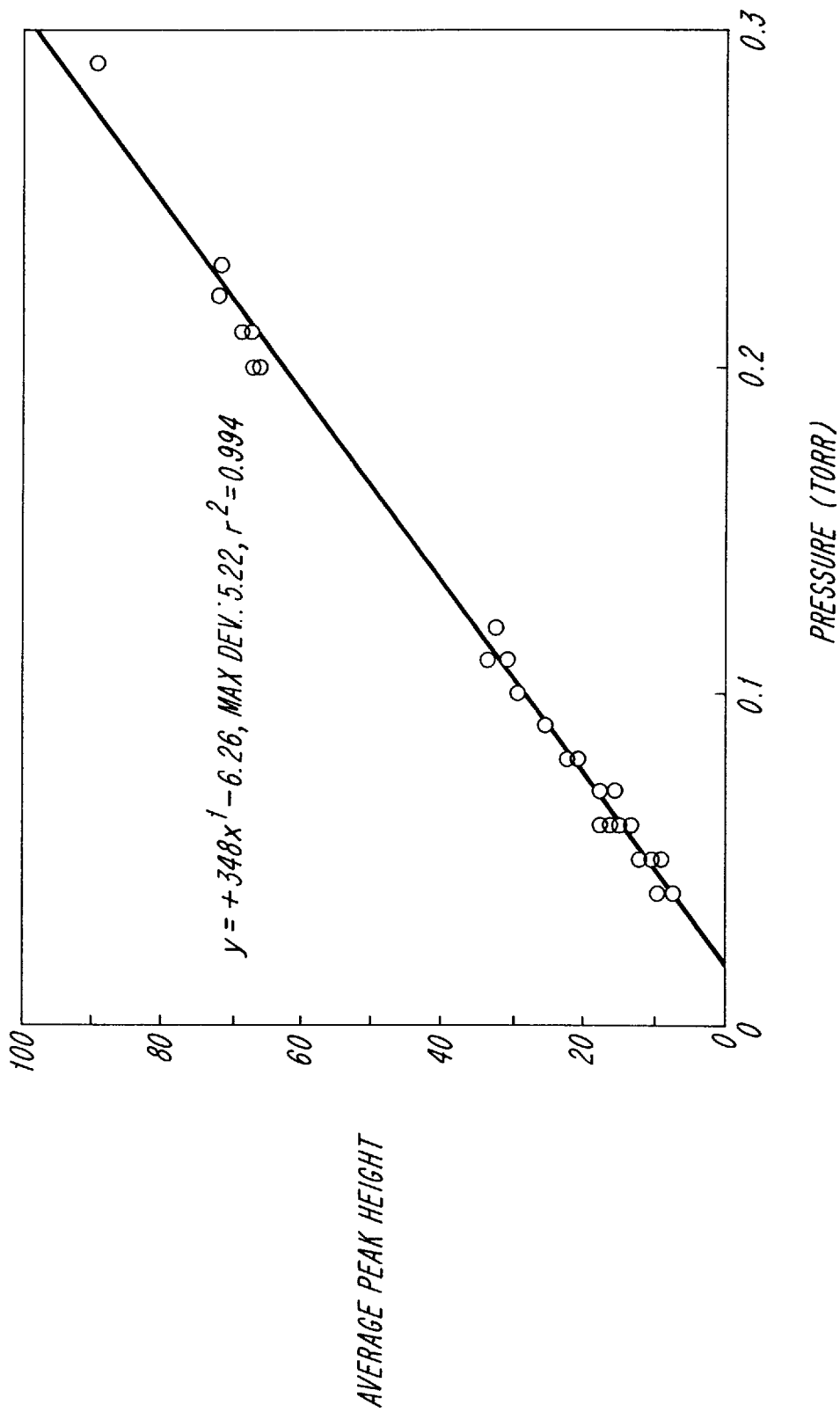
FIG. 6 is a graph showing absorption of diode laser light as a function of water vapor pressure.

The novel system described above allows for in situ detection of a molecular gas impurity, such as water vapor. In this regard, FIG. 6 illustrates the variation in absorption peak height of the light emitted by a diode laser at a wavelength of about 1.38 μm as a function of water vapor pressure at 27.8° C. These data were collected using second harmonic spectroscopy. This technique is discussed in copending applications, Ser. No. 08/711,646 filed on even date herewith, and Ser. No. 08/711,781, filed on even date herewith, The inventive system has particular applicability in detecting a molecular species in a gas exhausted from a vacuum chamber. In such a case, the cell can be disposed between a vacuum chamber and a vacuum pump system. The system is compatible with a wide range of materials. For example, the vacuum chamber can contain certain reactive or nonreactive (inert) gas species which can be in a plasma- or non-plasma state. Examples of reactive gases which are compatible with the inventive system include $SiH_4$, HCl and $Cl_2$ provided the moisture level is less than 1000 ppm. Any inert gas such as, e.g., $O_2$, $N_2$, Ar and $H_2$ can be used in the inventive system. In the case of the inventive system's use in a plasma environment, the system is preferably mounted about 6 inches or more away from the plasma zone in order to minimize the formation of deposits on the windows and other cell surfaces.

Because the detection system described above in reference to FIGS. 4A and 4B can be used in plasma or non-plasma atmospheres as well as with inert or reactive gases, the system is particularly well suited for use in monitoring gas phase molecular species, such as water vapor, in a semiconductor processing apparatus. Use of the detection system in conjunction with a semiconductor processing apparatus allows for real time in situ monitoring of gas phase molecular impurities. Additionally, because the cell height h and diameter d (See FIG. 3A and 3B) can be made arbitrarily small as described above, use of the cell in a semiconductor processing apparatus would not adversely affect operation of the apparatus or require costly alterations during retrofitting thereof.

Figure 5:
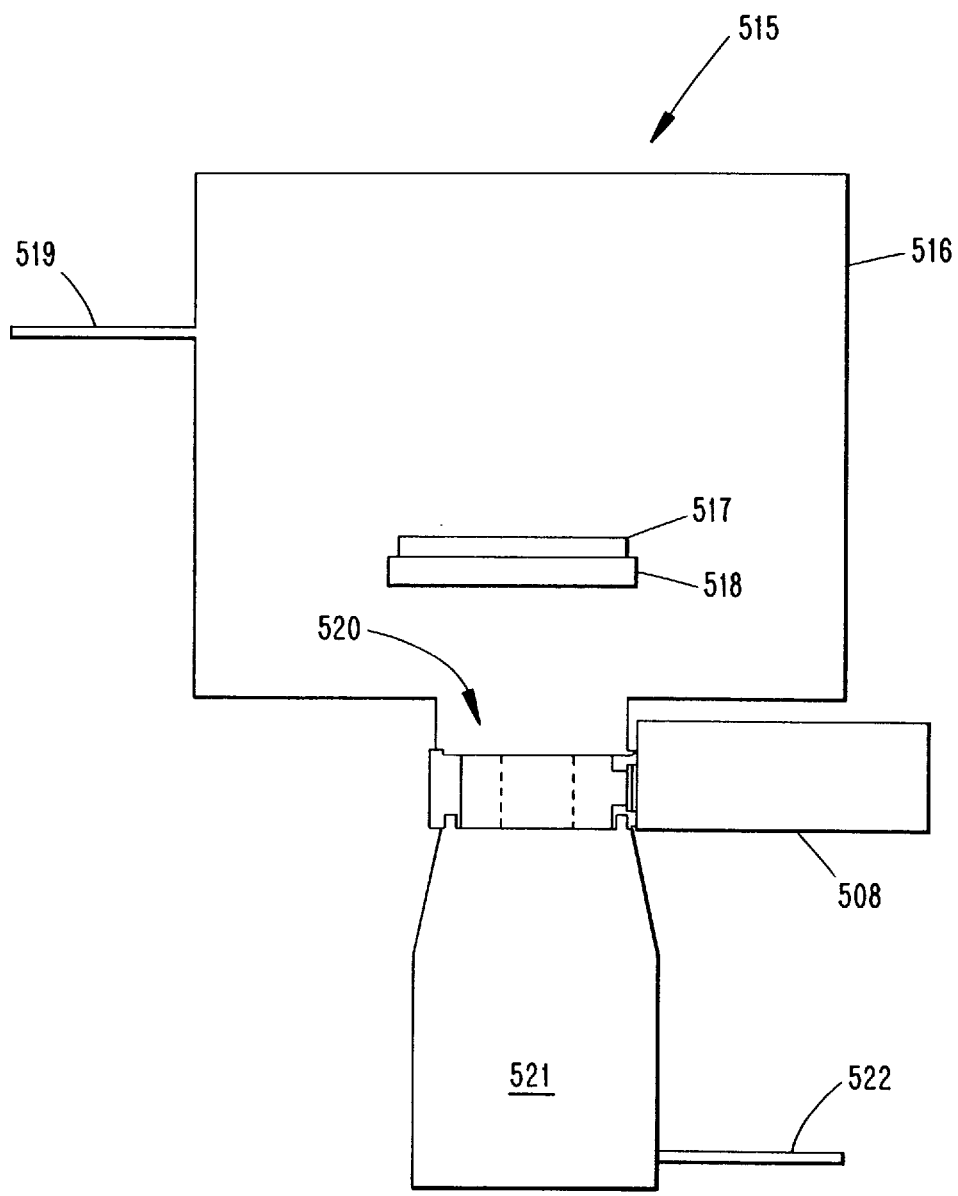
FIG. 5 is a side sectional view of a semiconductor processing apparatus which includes a system for detecting gas phase molecular species in a sample according to one embodiment of the present invention.

One example of such a configuration is shown in FIG. 5. While the structure of a semiconductor processing apparatus has been shown generically in FIG. 5, persons skilled in the art will appreciate that the system can be readily adapted to virtually any of the semiconductor processing apparatuses employing a vacuum system. Examples of such apparatuses are etching, diffusion, chemical vapor deposition (CVD), ion implantation, sputtering and rapid thermal processing apparatuses.

The apparatus 515 illustrated in FIG. 5 comprises a vacuum chamber 516 inside which a semiconductor substrate 517 is disposed on a substrate holder 518. A gas inlet 519 is provided for delivering a gas or plural gases to the vacuum chamber 516. The vacuum chamber is evacuated through an exhaust opening 520 in the vacuum chamber. A vacuum pump 521 for evacuating the vacuum chamber 516 is connected to the chamber, either directly or through a vacuum line, and a pump exhaust line 522 can be connected to the pump 521, which can be connected to another pump or to a gas scrubber (not shown). Examples of vacuum pumps which may be employed are mechanical rotary and booster pumps, diffusion pumps, cryogenic pumps, sorption pumps and turbomolecular pumps. The system for detecting gas phase molecules 508 has been described in detail above in reference to FIGS. 4A and 4B. While the vacuum pump 521 and the system for detecting gas phase molecules 508 have been illustrated as being disposed below the vacuum chamber 51, those skilled in the art readily understand that other orientations are also possible.

While the invention has been described in detail with reference to specific embodiments thereof, it will be apparent to one skilled in the art that various changes and modifications can be made, and equivalents employed, without departing from the scope of the appended claims.

We claim:

1. A polygonal planar multipass cell useful in absorption spectroscopy, comprising a sample region circumscribed by a plurality of walls, each wall having a light reflective surface facing the sample region, wherein each wall is connected to at least one other wall so as to form in cross-section substantially a polygon, at least one side of the polygon having a light entry/exit port therein, each entry/exit port containing a light transmissive window having a surface facing the sample region and disposed so as to seal the cell in the circumferential direction, the cell having a central axis parallel to the light reflective surfaces of the walls and the surface of each light transmissive window, which face the sample region.

2. The polygonal planar multipass cell according to claim 1, wherein the polygon is a regular polygon.

3. The polygonal planar multipass cell according to claim 2, wherein the regular polygon is an octagon.

4. The polygonal planar multipass cell according to claim 1, wherein the light reflecting surface of each wall is substantially planar.

5. The polygonal planar multipass cell according to claim 1, wherein the walls are arranged such that a light beam entering the cell remains in substantially the same plane while inside the cell.

6. The polygonal planar multipass cell according to claim 1, wherein the walls are arranged such that a light beam entering the cell is reflected from the light reflective surface of one wall to the light reflective surface of another wall, such that the light beam is reflected from each wall at least once prior to exiting the cell through the entry/exit port.

7. The polygonal planar multipass cell according to claim 1, wherein the cell has a height measured in a direction parallel to the cell central axis in the range of from approximately 1 to 5 cm.

8. The polygonal planar multipass cell according to claim 1, wherein the cell has a diameter in the range of from approximately 5 to 40 cm.

9. The polygonal planar multipass cell according to claim 1, wherein at least one of the at least one window has a coating on a surface opposite the surface facing the sample region for reflecting a portion of a light beam.

10. A system for detecting gas phase molecular species in a sample by absorption spectroscopy, comprising:

a polygonal planar multipass cell, comprising a sample region circumscribed by a plurality of walls, each wall having a light reflective surface facing the sample region, wherein each wall is connected to at least one other wall so as to form in cross-section substantially a polygon, at least one side of the polygon having a light entry/exit port therein, each entry/exit port containing a light transmissive window having a surface facing the sample region and disposed so as to seal the cell in the circumferential direction, the cell having a central axis parallel to the light reflective surfaces of the walls and the surface of each light transmissive window, which face the sample region;

a light source for directing a light beam through one of the at least one light transmissive windows into the cell, and a main detector for measuring the light beam exiting the cell through one of the at least one light transmissive windows, wherein a sample gas flows through the sample region in a direction parallel to the cell central axis.

11. The system for detecting gas phase molecular species according to claim 10, wherein the polygon is a regular polygon.

12. The system for detecting gas phase molecular species according to claim 10, wherein the absorption spectroscopy is tunable diode laser absorption spectroscopy.

13. The system for detecting gas phase molecular species according to claim 10, wherein the regular polygon is an octagon.

14. The system for detecting gas phase molecular species according to claim 10, wherein the light reflecting surface of each wall is substantially planar.

15. The system for detecting gas phase molecular species according to claim 10, wherein the light beam path in the cell is perpendicular to the cell central axis.

16. The system for detecting gas phase molecular species according to claim 10, wherein the walls are arranged such that the light beam remains in substantially the same plane while inside the cell.

17. The system for detecting gas phase molecular species according to claim 10, wherein the walls are arranged such that the light beam entering the cell is reflected from the light reflective surface of one wall to the light reflective surface of another wall, such that the light beam is reflected from each wall at least once prior to exiting the cell.

18. The system for detecting gas phase molecular species according to claim 10, wherein the cell has a height measured in a direction parallel to the cell central axis in the range of from approximately 1 to 5 cm.

19. The system for detecting gas phase molecular species according to claim 10, wherein the cell has a diameter measured in a direction perpendicular to the cell central axis in the range of from approximately 5 to 40 cm.

20. The system for detecting gas phase molecular species according to claim 10, wherein at least one of the at least one window has a coating on a surface opposite the surface facing the sample region for reflecting a portion of a light beam.

21. The system for detecting gas phase molecular species according to claim 10, further comprising a first mirror for reflecting the light beam from the light source through the light transmissive window into the cell, and a second mirror for reflecting the light beam exiting the cell to the main detector.

22. The system for detecting gas phase molecular species according to claim 10, further comprising a second detector for measuring a portion of the light beam which is reflected by the one of the at least one light transmissive windows.

23. The system for detecting gas phase molecular species according to claim 22, further comprising means for subtracting a reference signal provided by the second detector from a measurement obtained by the main detector.

24. The system for detecting gas phase molecular species according to claim 10, wherein the cell is disposed between and in communication with a vacuum chamber and a vacuum pump.

25. The system for detecting gas phase molecular species according to claim 24, wherein the vacuum chamber forms a portion of a semiconductor processing apparatus.

26. The system for detecting gas phase molecular species according to claim 25, wherein the semiconductor processing apparatus is selected from the group consisting of an etching apparatus, a chemical vapor deposition apparatus, an ion implantation apparatus, a sputtering apparatus and a rapid thermal processing apparatus.

27. The system for detecting gas phase molecular species according to claim 26, wherein the semiconductor processing apparatus is an etching apparatus.

28. The system for detecting gas phase molecular species according to claim 10, wherein the vacuum chamber is adapted to contain a plasma atmosphere.

29. The system for detecting gas phase molecular species according to claim 10, wherein the vacuum chamber is adapted to contain a reactive gas atmosphere.

30. A semiconductor processing apparatus, comprising:

a vacuum chamber in communication with a vacuum pump for evacuating the vacuum chamber, a polygonal planar multipass cell useful for absorption spectroscopy disposed between and in communication with the vacuum chamber and the vacuum pump, the cell comprising a sample region circumscribed by a plurality of walls, each wall having a light reflective surface facing the sample region, wherein each wall is connected to at least one other wall so as to form in plan substantially a polygon, at least one side of the polygon having a light entry/exit port therein, each entry/exit port containing a light transmissive window having a surface facing the sample region and disposed so as to seal the cell in the circumferential direction, the cell having a central axis parallel to the light reflective surfaces of the walls and the surface of each light transmissive window, which face the sample region;

and further comprising a light source for directing a light beam through one of the at least one light transmissive windows into the cell, and a main detector for measuring the light beam exiting the cell through one of the at least one light transmissive windows, wherein a sample gas flows through the sample region in a direction parallel to the cell central axis.

31. A method of detecting gas phase molecular species using a polygonal planar multipass cell useful in absorption spectroscopy, the cell comprising a sample region circumscribed by a plurality of walls, each wall having a light reflective surface facing the sample region, wherein each wall is connected to at least one other wall so as to form in cross-section substantially a polygon, at least one side of the polygon having a light entry/exit port therein, each entry/exit port containing a light transmissive window having a surface facing the sample region and disposed so as to seal the cell in the circumferential direction, the cell having a central axis parallel to the light reflective surfaces of the walls and the surface of each light transmissive window, which face the sample region, the method comprising the steps of:

directing a light beam through at least one of the at least one light transmissive windows into the sample region of the cell which contains a gas sample, wherein the light beam remains in substantially the same plane while inside the cell; and measuring the light beam which exits the cell through at least one of the at least one light transmissive windows.

32. The method for detecting gas phase molecular species according to claim 31, wherein the light beam is reflected from the light reflective surface of one wall to the light reflective surface of another wall, such that the light beam is reflected from each wall at least once prior to exiting the cell through one of the at least one light transmissive windows.

33. The method for detecting gas phase molecular species according to claim 31, wherein the gas sample flows through the cell.

34. The method for detecting gas phase molecular species according to claim 33, wherein the gas sample comprises a gas exhausted from a vacuum chamber, and wherein the gas phase molecular species is detected in situ.

35. The method for detecting gas phase molecular species according to claim 31, wherein the molecular gas impurity is water vapor.

36. The method for detecting gas phase molecular species according to claim 31, further comprising measuring a portion of the light beam which is reflected by the at least one of the at least one light transmissive windows through which the light beam is directed into the cell, and subtracting the measured signal due to the reflected light beam from a signal due to the portion of the light beam which exits the cell.

37. The method for detecting gas phase molecular species according to claim 31, wherein the cell is disposed between and in communication with a vacuum chamber and a vacuum pump.

38. The method for detecting gas phase molecular species according to claim 37, wherein the vacuum chamber forms a portion of a semiconductor processing apparatus.

39. The method for detecting gas phase molecular species according to claim 38, wherein the semiconductor processing apparatus is an etching apparatus.

40. The method for detecting gas phase molecular species according to claim 37, wherein the semiconductor processing apparatus is selected from the group consisting of an etching apparatus, a chemical vapor deposition apparatus, an ion implantation apparatus, a sputtering apparatus and a rapid thermal processing apparatus.

41. The method for detecting gas phase molecular species according to claim 31, wherein the vacuum chamber contains a plasma atmosphere.

42. The method for detecting gas phase molecular species according to claim 31, wherein the vacuum chamber contains a reactive gas atmosphere.

* * * * *